US006525234B1

(12) United States Patent
Dandekar et al.

(10) Patent No.: US 6,525,234 B1
(45) Date of Patent: Feb. 25, 2003

(54) PROCESS FOR LIQUID PHASE AROMATICS ALKYLATION COMPRISING IN-SITU CATALYST REACTIVATION WITH POLAR COMPOUNDS

(75) Inventors: Ajit B. Dandekar, Marlton, NJ (US); Thomas Francis Degnan, Moorestown, NJ (US); John P. McWilliams, Woodbury, NJ (US); Chaya R. Venkat, Princeton, NJ (US)

(73) Assignee: ExxonMobil Oil Corporation, Fairfax, VA (US)

( * ) Notice: Subject to any disclaimer, the term of this patent is extended or adjusted under 35 U.S.C. 154(b) by 0 days.

(21) Appl. No.: 09/717,705

(22) Filed: Nov. 21, 2000

(51) Int. Cl.⁷ ............................................. C07C 2/68
(52) U.S. Cl. ..................................................... 585/467
(58) Field of Search ........................... 585/467; 502/22, 502/27, 28, 29, 33

(56) References Cited

U.S. PATENT DOCUMENTS

| | | | |
|---|---|---|---|
| 2,541,044 A | 8/1951 | Daughetry | 260/671 |
| 3,148,155 A | 9/1964 | Schwartz et al. | 252/413 |
| 3,293,192 A | 12/1966 | Maher et al. | 252/430 |
| 3,308,069 A | 3/1967 | Wadlinger et al. | 252/455 |
| 3,442,795 A | 5/1969 | Kerr et al. | 208/120 |
| 3,449,070 A | 6/1969 | McDaniel et al. | 23/111 |
| 3,702,886 A | 11/1972 | Argauer et al. | 423/328 |
| 3,709,979 A | 1/1973 | Chu et al. | 423/328 |
| 3,832,449 A | 8/1974 | Rosinski et al. | 423/328 |
| 3,923,636 A | 12/1975 | Mead et al. | 208/58 |
| 3,972,983 A | 8/1976 | Ciric | 423/328 |
| 4,016,218 A | 4/1977 | Haag et al. | 260/671 |
| 4,016,245 A | 4/1977 | Plank et al. | 423/328 |
| 4,076,842 A | 2/1978 | Plank et al. | 423/328 |
| 4,234,231 A | 11/1980 | Yan | 299/4 |
| 4,276,149 A | 6/1981 | Chester et al. | 208/120 |
| 4,319,057 A | 3/1982 | Kiser | 568/916 |
| 4,365,104 A | 12/1982 | Kaeding | 585/467 |
| 4,401,556 A | 8/1983 | Bezman et al. | 208/111 |
| 4,418,235 A | 11/1983 | Haag et al. | 585/407 |
| 4,429,176 A | 1/1984 | Chester et al. | 585/481 |
| 4,439,409 A | 3/1984 | Puppe et al. | 423/328 |
| 4,477,585 A | 10/1984 | Kaeding | 502/77 |
| 4,486,616 A * | 12/1984 | Chu et al. | 585/466 |
| 4,490,570 A | 12/1984 | Forward et al. | 585/467 |
| 4,522,929 A | 6/1985 | Chester et al. | 502/77 |
| 4,550,090 A | 10/1985 | Degnan et al. | 502/25 |
| 4,556,477 A | 12/1985 | Dwyer | 208/111 |
| 4,594,146 A | 6/1986 | Chester et al. | 208/111 |
| 4,663,492 A | 5/1987 | Chester et al. | 585/408 |
| 4,678,764 A | 7/1987 | Le et al. | 502/26 |
| 4,992,606 A | 2/1991 | Kushnerick et al. | 585/467 |
| 5,077,445 A | 12/1991 | Le | 585/467 |
| 5,149,894 A | 9/1992 | Holtermann et al. | 585/467 |
| 5,191,135 A | 3/1993 | Dwyer et al. | 585/455 |
| 5,236,575 A | 8/1993 | Bennett et al. | 208/46 |
| 5,250,277 A | 10/1993 | Kresge et al. | 423/329.1 |
| 5,258,565 A | 11/1993 | Kresge et al. | 585/467 |
| 5,292,698 A | 3/1994 | Chu et al. | 502/84 |
| 5,334,795 A | 8/1994 | Chu et al. | 585/467 |
| 5,362,697 A | 11/1994 | Fung et al. | 502/71 |
| 5,371,310 A | 12/1994 | Bennett et al. | 585/467 |
| 5,425,934 A | 6/1995 | Malla et al. | 423/714 |
| 5,453,554 A | 9/1995 | Cheng et al. | 585/467 |
| 5,493,065 A * | 2/1996 | Cheng et al. | 585/467 |
| 5,557,024 A | 9/1996 | Cheng et al. | 585/467 |

FOREIGN PATENT DOCUMENTS

WO   WO 93/00992   * 1/1993

* cited by examiner

Primary Examiner—Thuan D. Dang
(74) Attorney, Agent, or Firm—Darryl M. Tyus

(57) ABSTRACT

A process for alkylating aromatics comprises:

i) contacting a feed containing alkylatable aromatic, e.g., benzene, under liquid phase alkylating conditions with an alkylating agent, e.g., ethylene, in the presence of an alkylation catalyst comprising a porous crystalline material, e.g., MCM-22, to provide an alkylated aromatic product during which contacting said catalyst becomes at least partially deactivated by sorbing catalyst poisons present in said feed;

ii) treating said at least partially deactivated catalyst in situ by contacting with at least one polar compound, e.g., water or acetic acid, having a dipole moment of at least 0.05 Debyes under conditions of temperature and pressure employed in said liquid phase alkylating conditions which are sufficient to at least partially desorb said catalyst poison from said catalyst; and iii) collecting said alkylated aromatic product.

6 Claims, No Drawings

PROCESS FOR LIQUID PHASE AROMATICS ALKYLATION COMPRISING IN-SITU CATALYST REACTIVATION WITH POLAR COMPOUNDS

FIELD OF THE INVENTION

The present invention relates to a process for alkylating aromatics.

BACKGROUND OF THE INVENTION

Zeolite and other porous crystalline molecular sieve catalysts are increasingly being used in low temperature, liquid phase aromatic alkylation processes including ethylbenzene, cumene, and linear polyalkylbenzene (LAB) synthesis. Operation at lower temperatures improves process economics and, in many cases, product selectivity. However, trace feed impurities such as low molecular weight nitrogen, sulfur, and oxygen compounds, which are not strongly adsorbed in higher temperature vapor phase alkylation processes, are more problematic in the liquid phase processes. The affinity of these compounds for the active sites in the molecular sieve catalyst can cause rapid deactivation by displacing or neutralizing the acid site.

There are numerous methods known for reactivating catalysts. U.S. Pat. No. 2,541,044 to Daugherty discloses catalytic alkylation with simultaneous restoration of the alkylation catalyst activity by contacting the catalyst with an alkylatable hydrocarbon while interrupting the flow of alkylating agent. U.S. Pat. No. 3,148,155 to Schwartz describes removing metal poisons from cracking catalysts by contacting the poisoned catalyst with an aqueous solution of sulfurous acid, a water-soluble salt of sulfurous acid or a water-soluble salt of hyposulfurous acid. U.S. Pat. No. 4,418,235 to Haag discloses aromatic alkylation in the presence of steam to enhance or preserve zeolite catalyst activity. U.S. Pat. No. 4,550,090 to Degnan et al. describes a method for displacing high molecular weight poisons from ZSM-5 catalysts, such as those used in dewaxing, by in-situ treatment with more easily desorbed compounds such as ammonia or by treatment with alkali or alkaline metal cations to effect ion exchange. U.S. Pat. No. 4,276,149 to Chester et al. describes passivating metal contaminants on zeolite cracking catalysts by contacting with steam for limited periods. U.S. Pat. No. 4,678,764 to Le et al. discloses reactivation of noble metal-containing zeolites poisoned with sulfur oxides by contacting with aqueous acid solutions, e.g., nitric, carbon, acetic and formic acids. U.S. Pat. No. 4,319,057 to Kiser discloses regenerating molecular sieve dehydration materials with methanol or acetone. U.S. Pat. No. 5,425,934 to Malla et al. teaches treating zeolites with methanol, ethanol or propanol plus nitric or sulfuric acid for the removal of organic templates. U.S. Pat. Nos. 4,365,104 and 4,477,585 to Kaeding disclose enhancing para-selectivity of zeolite alkylation catalysts by treatment with hydrogen sulfide or carbon dioxide. U.S. Pat. 4,490,570 to Forward et al. discloses para-selective alkylation of a monoalkylbenzene wherein water in the form of steam can be co-fed with the reactants. U.S. Pat. No. 5,077,445 to Le discloses a process for liquid-phase synthesis of an alkylbenzene, such as ethylbenzene, using MCM-22 zeolite catalyst hydrated with liquid water. U.S. Pat. No. 5,191,135 to Dwyer et al. discloses preparing long chain alkyl substituted aromatic compounds by alkylating naphthalenes with $C_{6+}$ alkylating agent in the presence of large pore size zeolite such as USY and MCM-22 in the presence of 0.5 to 3.0 wt % co-fed water to increase selectivity to monoalkyl-substituted products.

All of the above patents are incorporated in their entirety herein by reference.

It would be desirable to provide a process for reactivating liquid phase alkylation catalysts which have been contaminated by trace quantities of strongly sorbed poisons. It would be especially useful to provide a method for reactivating such catalysts in-situ by treatment with species that are introduced along with the liquid phase or vapor phase feed streams.

SUMMARY OF THE INVENTION

In one aspect, the present invention relates to a process for alkylating aromatics which comprises:

i) contacting a feed containing alkylatable aromatic under liquid phase alkylating conditions with an alkylating agent of no greater than 5 carbon atoms in the presence of an alkylation catalyst comprising a porous crystalline material, to provide an alkylated aromatic product during which contacting said catalyst becomes at least partially deactivated by sorbing catalyst poisons present in said feed;

ii) treating said catalyst in situ by contacting with at least one polar compound having a dipole moment of at least 0.05 Debyes under conditions of temperature and pressure employed in said liquid phase alkylating conditions which are sufficient to at least partially desorb said catalyst poison from said catalyst; and iii) collecting said alkylated aromatic product.

In another aspect, the present invention relates to a process for alkylating aromatics which comprises:

1) contacting a feed containing alkylatable aromatic under liquid phase alkylating conditions with alkylating agent in the presence of an alkylation catalyst comprising a porous crystalline material to provide an alkylated aromatic product during which contacting said catalyst becomes at least partially deactivated by sorbing catalyst poisons present in said feed;

2) treating said catalyst in situ by contacting with at least one non-aqueous polar compound having a dipole moment of at least 0.05 Debyes under conditions of temperature and pressure employed in said liquid phase alkylating conditions which are sufficient to at least partially desorb said catalyst poison from said catalyst; and 3) collecting said alkylated aromatic product.

The above and other objects, features and advantages of the present invention will be better understood from the following detailed descriptions, all of which are given by illustration only, and are not limitative of the present invention.

DETAILED DESCRIPTION OF THE INVENTION

Alkylation Catalysts

Acidic solid oxides which may be used to catalyze the present alkylation reaction include PSH-3, SSZ-25, MCM-22, MCM-36, MCM49 and MCM-56. PSH-3 is described in U.S Pat. No. 4,439,409. SSZ-25 and its use in aromatics alkylation is described in U.S. Pat. No. 5,149,894. MCM-22 and its use to catalyze the synthesis of alkylaromatics, including ethylbenzene, is described in U.S. Pat. Nos. 4,992,606; 5,077,445; and 5,334,795. MCM-36 is described in U.S. Pat. Nos. 5,250,277 and 5,292,698. U.S. Pat. No.

5,258,565 describes the synthesis of alkylaromatics, including ethylbenzene, using a catalyst comprising MCM-36. MCM-49 is described in U.S Pat. No. 5,236,575. The use of MCM49 to catalyze the synthesis of alkylaromatics, including ethylbenzene, is described in U.S. Pat. Nos. 5,493,065 and 5,371,310. MCM-56 is described in U.S. Pat. No. 5,362,697. The use of MCM-56 to catalyze the synthesis of alkylaromatics including ethylbenzene is described in U.S. Pat. Nos. 5,557,024 and 5,453,554. A preferred group of catalysts for use in the present invention is selected from the group consisting of MCM-22, MCM-36, MCM-49 and MCM-56, and most preferably, MCM-22.

Alternative catalysts suitable for use herein include medium pore zeolites having a Constraint Index of 2-12 (as defined in U.S. Pat. No. 4,016,218), such as ZSM-5, ZSM-11, ZSM-12, ZSM-22, ZSM-23, ZSM-35, and ZSM-48. ZSM-5 is described in detail in U.S. Pat. No. 3,702,886. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM48 is more particularly described in U.S. Pat. No. 4,234,231.

In addition, large pore zeolites, including those zeolites having a Constraint Index less than 2, are suitable for use as the catalyst in the process of the invention. Suitable large pore zeolites include zeolite Beta, zeolite Y, Ultrastable Y (USY), Dealuminized Y (Deal Y), mordenite, offretite, ZSM-3, ZSM-4, ZSM-18, and ZSM-20. Zeolite ZSM-4 is described in U.S. Pat. No. 3,923,636. Zeolite ZSM-20 is described in U.S. Pat. No. 3,972,983. Zeolite Beta is described in U.S. Pat. Nos. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556.

The zeolite crystals employed in the present invention can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

The crystalline material may be composited with another material which is resistant to the temperatures and other conditions employed in the alkylation process of this invention. Such materials include active and inactive materials and synthetic or naturally occurring zeolites as well as inorganic materials such as clays and/or oxides such as alumina, silica or silica-alumina. The latter may be either naturally occurring or in the form of gelatinous precipitates or gels including mixtures of silica and metal oxides. Use of a material in conjunction with the zeolite, i.e., combined therewith or present during its synthesis, which itself is catalytically active may change the conversion and/or selectivity of the catalyst. Inactive materials suitably serve as diluents to control the amount of conversion so that alkylation products can be obtained economically and in an orderly manner without employing other means for controlling the rate of reaction These materials may be incorporated into naturally occurring clays, e.g., bentonite and kaolin, to improve the crush strength of the catalyst under commercial alkylation operating conditions and function as binders or matrices for the catalyst. The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The stability of the catalyst used in the present process may be increased by steaming. U.S. Pat. Nos. 4,663,492; 4,594,146; 4,522,929; and 4,429,176, describe conditions for the steam stabilization of zeolite catalysts which can be utilized to steam-stabilize the catalyst. Reference is made to these patents for a detailed description of the steam stabilization technique for use with the present catalysts. The steam stabilization conditions typically include contacting the catalyst with, e.g., 5-100% steam at a temperature of at least about 300° C. (e.g., 300°–650° C.) for at least one hour (e.g., 1–200 hours) at a pressure of 101–2,500 kPa. In a more particular embodiment, the catalyst can be made to undergo steaming with 75–100% steam at 315°–500° C. and atmospheric pressure for 2–25 hours. The steaming of the catalyst can take place under conditions sufficient to initially increase the Alpha Value of the catalyst, the significance of which is discussed below, and produce a steamed catalyst having an enhanced Alpha Value. If desired, steaming can be continued to subsequently reduce the Alpha Value from the higher Alpha Value to an Alpha Value which is substantially the same as the Alpha Value of the unsteamed catalyst.

Reactants

The reactants used in the process of the invention include an alkylatable aromatic compound and an alkylating agent.

The term "aromatic" in reference to the alkylatable compounds that are useful herein is to be understood in accordance with its art-recognized scope that includes alkyl substituted and unsubstituted mono- and polynuclear compounds. Compounds of an aromatic character, which possess a heteroatom, are also useful provided they do not act as catalyst poisons under the reaction conditions selected.

Substituted aromatic compounds that can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups that do not interfere with the alkylation reaction.

Suitable aromatic hydrocarbons include benzene, toluene, naphthalene, anthracene, naphthacene, perylene, coronene, and phenanthrene, with benzene being preferred.

Generally the alkyl groups that can be present as substituents on the aromatic compound contain from about 1 to 22 carbon atoms, usually from about 1 to 8 carbon atoms, and most usually from about 1 to 5 carbon atoms.

The alkylating agents that are useful in the process of this invention generally include any aliphatic or aromatic organic compound having one or more available alkylating aliphatic groups capable of reaction with the alkylatable aromatic compound. Examples of suitable alkylating agents are $C_2$–$C_{16}$ olefins such as $C_2$–$C_5$ olefins, viz., ethylene, propylene, the butenes, and the pentenes; $C_1$–$C_{12}$ alkanols (inclusive of monoalcohols, dialcohols, trialcohols, etc.), preferably $C_1$–$C_5$ alkanols, such as methanol, ethanol, the propanols, the butanols, and the pentanols; $C_2$–$C_{20}$ ethers, e.g., $C_2$–$C_5$ ethers including dimethylether and diethylether; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth. It is generally preferred that the alkylating agent has no greater than 5 carbon atoms, more preferably no greater than 3 carbon atoms. Thus the alkylating agent can preferably be selected from the group consisting of $C_2$–$C_5$ olefins and $C_1$–$C_5$ alkanols.

Mixtures of light olefins are especially useful as alkylating agents in the alkylation process of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents herein. For example, a typical FCC light olefin stream possesses the following composition:

|  | Wt. % | Mole % |
| --- | --- | --- |
| Ethane | 3.3 | 5.1 |
| Ethylene | 0.7 | 1.2 |
| Propane | 4.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

The feed comprising reactants of the present process can contain catalyst poisons. Such materials while present in trace amounts can cause deactivation of the alkylation catalyst over time. Catalyst poisons which are strongly sorbed to the alkylation catalyst under liquid phase alkylation conditions include nitrogen compounds, sulfur compounds and oxygen compounds of low molecular weight, say, no greater than 500, preferably no greater than 300. Such catalyst poison compounds can include ammonia, alkylamines, e.g., methylamine and n-propylamine, N-formyl morpholine and N-methyl pyrrolidine. These catalyst poisons can make up to 100 ppm of the total feed to the process, e.g., 0.001 to 100 ppm.

Products

Suitable alkyl substituted aromatic compounds which can be prepared from the alkylation process of the present invention include toluene, xylene, isopropylbenzene (cumene), normal propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethyinaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Preferably, the alkylated aromatic product comprises monoalkylbenzene. Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecyltoluene, etc. Very often alkylate is obtained as a high boiling fraction in which the alkyl group attached to the aromatic nucleus varies in size from about $C_6$ to about $C_{16}$.

Reaction Conditions

In general, the alkylation reactions of the present invention take place under liquid phase conditions, i.e., at least one of the reactants being in the liquid phase. The liquid phase alkylating conditions can comprise temperatures ranging from 100° to 400° C., preferably from 100° to 300° C., pressures ranging from 0.2 to 25 atmospheres, preferably ranging from 1 to 5 atmospheres, a WHSV of from 0.1 to 10, preferably from 0.5 to 5 and an alkylatable aromatic compound to alkylating agent mole ratio of from about 0.1:1 to 50:1, preferably from 0.5:1 to 5:1.

More specifically, liquid phase alkylation of benzene with ethylene may be carried out at temperatures between 300° and 650° F. (150° to 340° C.) usually in the range of 400° to 520 F. (205° to 270° C.). Pressures during the liquid phase alkylation of benzene with ethylene may be as high as about 3000 psig (20875 kPa) although generally will not exceed 1000 psig (7000 kPa). The reaction may be carried out in the absence of hydrogen and accordingly the prevailing pressures are those of the reactant species. The space velocity may be from about 0.1 to 20 WHSV, based on the ethylene feed. Preferred space velocities for the liquid phase alkylation of benzene with ethylene include ranges, for example, from about 0.5 to about 3 WHSV, e.g., from about 0.75 to 2.0 WHSV, (ethylene). The ratio of the benzene to the ethylene in the alkylation reactor may be from 1:1 to 30:1 molar, normally about 5:1 to 20:1 molar, say from about 5:1 to 10:1 molar.

Polar Compound Reactivating Agent

Polar compounds suited for use in the present invention exhibit a dipole moment of greater than 0.05 Debyes (D), preferably greater than 0.1 Debyes. The polar compounds employed in the present process can be selected from the group consisting of water, carbon monoxide, carbon dioxide, hydrogen sulfide, dimethyl disulfide, sulfuric acid, carbonic acid, acetic acid, methanol, ethanol, 1-propanol, 2-propanol, n-butanol, nitric acid, formic acid, and acetone. Preferably, the polar compound is selected from the group consisting of water, acetic acid, carbonic acid, nitric acid and sulphuric acid. The polar compound can be a non-aqueous compound. Alternatively, the polar compound can be selected from the group of inorganic compounds, e.g., non-aqueous inorganic compounds.

The polar compound suited to use in the present invention is capable of displacing sorbed catalyst poisons from active sites of the alkylation catalyst under conditions, e.g., temperatures and pressures, encountered during alkylation. The displacing polar compound has a less deleterious effect upon catalyst activity and/or selectivity than the catalyst poison, producing a net improvement in catalyst activity and/or selectivity. The displaced poisons may remain on the catalyst in a less problematic state or, preferably, they may be expelled from a catalyst bed as the added polar compound permeates the catalyst bed.

Inasmuch as the catalyst is exposed to the polar compound in situ, the present invention can permit reactivation of catalysts without removal of the catalyst from the process vessel, ideally while the catalyst is still at temperature and processing feed. The feed contacting step and catalyst treatment step can be carried out simultaneously by cofeeding the feed and the polar compound. Thus, the present invention permits reactivation of catalysts while the alkylation process is still operating, and eliminates the need for costly shutdown to effect catalyst regeneration.

The present invention can also utilize polar compounds as "off-line" reactivation agents when it is desired to shut the unit down and reactivate the catalyst in situ, i.e., while the catalyst is in the reactor. Thus the feed contacting step and catalyst treatment step can be carried out serially, i.e., the feed contacting step and catalyst treatment step are carried out one after the other, non-simultaneously.

The polar compound to effect catalyst reactivation should be added in an amount sufficient to displace catalyst poison under liquid phase alkylation conditions. During simultaneous cofeeding of reactants and polar compound, the polar compound should be added in amounts of at least 0.01 ppm, preferably 0.1 ppm, say 0.1 to 100 ppm of total feed to the alkylation process. During serial operation, polar compound should be added in amounts of at least 0.01 wt. % of total catalyst weight, preferably at least 0.05 wt. %, e.g., 0.05 to 5 wt. % of total catalyst weight. Such an amount can be added over periods ranging from 0.1 to 72 hours, preferably from 0.2 to 24 hours.

All of the patents noted above are incorporated herein by reference in their entirety.

The following examples will serve to further illustrate processes and some advantages of the present invention.

EXAMPLE 1

Ethylbenzene Synthesis from Benzene and Ethylene Over MCM-22

MCM-22 catalyst was prepared by extruding 65 wt. % MCM-22 crystal with 35 wt. % alumina into 1/16" extrudate. The basic nitrogen content of the catalyst was evaluated using an established commercial analytical technique. 10 g of the catalyst were charged to an isothermal well-mixed Parr autoclave reactor along with a mixture comprising benzene (195 g) and ethylene (20 g). The reaction was carried out at 428° F. (220° C.) and 550 psig (3900 kPa) for 4 hours. A small sample of the product was withdrawn at regular intervals and analyzed by gas chromatography. The catalyst performance was assessed by a kinetic activity rate constant (EBA) based on ethylene conversion and ethylbenzene selectivity at 100% ethylene conversion, and is described in Example 5.

EXAMPLE 2

Ethylbenzene Synthesis from Benzene and Ethylene Over MCM-22 Impregnated with n-Propyl Amine 4.2 g of n-propyl amine were dissolved in 172 g of benzene. The resulting solution was used to impregnate 200 g of a fresh sample of MCM-22 using an incipient wetness method. The impregnated catalyst was dried at 250° F. (121° C.) for 12 hours in air. The basic nitrogen content of the finished catalyst was then evaluated. 10 g of the final catalyst were also evaluated for benzene alkylation with ethylene according to the procedure described in Example 1. Catalyst performance is compared with MCM-22 in Example 5.

EXAMPLE 3

Ethylbenzene Synthesis from Benzene and Ethylene Over MCM-22 Impregnated with n-Propyl Amine and Subjected to Steam Treatment 20 g of finished catalyst from Example 2 were subjected to 50 ml/minute of steam at 302° F. (150° C.) at atmospheric pressure for 24 hours. The basic nitrogen content of the finished catalyst was then evaluated. 10 g of the final catalyst were also evaluated for benzene alkylation with ethylene according to the procedure described in Example 1. Catalyst performance is compared with MCM-22 in Example 5.

EXAMPLE 4

Ethylbenzene Synthesis from Benzene and Ethylene Over MCM-22 Impregnated with n-Propyl Amine and Subjected to HOAc Treatment 20 g of finished catalyst from Example 2 were subjected to 100 ml of 0.1M acetic acid solution at 200° F. (80° C.) at atmospheric pressure for 1 hour in a beaker with constant stirring. The treatment was repeated thrice using fresh acetic acid solution each time. The catalyst was then dried in air at 250° F. (121° C.) for 12 hours. The basic nitrogen content of the finished catalyst was then evaluated. 10 g of the final catalyst were also evaluated for benzene alkylation with ethylene according to the procedure described in Example 1. Catalyst performance is compared with MCM-22 in Example 5.

EXAMPLE 5

Comparison of Catalyst Properties and Performance

The performance of MCM-22 doped with n-propylamine and then pretreated according to procedures described in Examples 2–4 is compared with MCM-22 in the Table below. The data represent basic nitrogen content of each catalyst, activity for ethylbenzene synthesis and selectivity to di- and triethylbenzenes at 100% ethylene conversion.

TABLE

| Catalyst | Nitrogen Content (ppm) | Ethylbenzene Activity | DiEB/EB (wt %) |
|---|---|---|---|
| Example 1 | 5 | 43 | 8.5 |
| Example 2 | 5800 | 6 | Non-detectable |
| Example 3 | 4500 | 20 | 8.7 |
| Example 4 | 2800 | 30 | 8.7 |

It is claimed:

1. A process for alkylating aromatics which comprises:
   i) contacting a feed containing alkylatable aromatic under liquid phase alkylating conditions with alkylating agent in the presence of an alkylation catalyst comprising a porous crystalline material to provide an alkylated aromatic product, during which contacting said catalyst becomes at least partially deactivated by sorbing catalyst poisons present in said feed;
   ii) treating said at least partially deactivated catalyst in situ by contacting with at least one non-aqueous polar compound having a dipole moment of at least 0.05 Debyes under conditions of temperature and pressure employed in said liquid phase alkylating conditions which are sufficient to at least partially desorb said catalyst poison from said catalyst; and
   iii) collecting said alkylated aromatic product,
   wherein said alkylatable aromatic is benzene, toluene, xylenes, alkylbenzenes, naphthalene or substituted naphthalenes, said alkylating agent is $C_2$–$C_{16}$ olefins, said liquid phase alkylating conditions comprise temperatures ranging from 100° to 400° C., pressures ranging from 0.2 to 25 atmospheres, an WHSV of from 0.1 to 10 and an alkylatable aromatic compound to alkylating agent mole ratio of from about 0.1:1 to 50:1, said polar compound is carbon dioxide, hydrogen sulfide, dimethyl disulfide, sulfuric acid, carbonic acid, methanol, ethanol, isopropanol, n-propanol, n-butanol, nitric acid, or acetone, said porous crystalline material is MCM-22, MCM-36, MCM-49, MCM-56, ZSM-5, ZSM-11, ZSM-12, ZSM-23, ZSM-35, ZSM-48, ZSM-50, ZSM-4, ZSM-18, ZSM-20, Zeolite X, Zeolite Y, USY, mordenite or offretite.

2. The process of claim 1 wherein said polar compound is selected from the group consisting of, carbonic acid, nitric acid and sulfuric acid.

3. The process of claim 1 wherein said steps 1) and 2) are carried out simultaneously by cofeeding said feed and said polar compound.

4. The process of claim 1 wherein said steps 1) and 2) are carried out serially.

5. The process of claim 1 wherein said alkylating agent has no greater than 5 carbon atoms.

6. The process of claim 1 wherein said alkylatable aromatic is benzene or toluene, said alkylating agent is $C_2$–$C_5$ olefins, said liquid phase alkylating conditions comprise temperatures ranging from 100° to 300° C., pressures ranging from 1 to 5 atmospheres, a WHSV of from 0.5 to 5 and an alkylatable aromatic compound to alkylating agent mole ratio of from about 0.5:1 to 5:1, said polar compound is carbon dioxide, hydrogen sulfide, dimethyl disulfide, sulfuric acid, carbonic acid, methanol, ethanol, isopropanol, n-propanol, n-butanol, nitric acid, or acetone, and said porous crystalline material is MCM-22, MCM-36, MCM-49 or MCM-56.

\* \* \* \* \*